United States Patent
Ellis et al.

(10) Patent No.: US 10,745,644 B1
(45) Date of Patent: Aug. 18, 2020

(54) **POST PROCESSING METHOD FOR *CANNABIS* OIL**

(71) Applicant: CRESCO LABS LLC, Chicago, IL (US)

(72) Inventors: David Ellis, Chicago, IL (US); Tamer Mohamed, Chicago, IL (US)

(73) Assignee: CRESCO LABS LLC, Chicago, IL (US)

( * ) Notice: Subject to any disclaimer, the term of this patent is extended or adjusted under 35 U.S.C. 154(b) by 0 days.

(21) Appl. No.: 16/728,521

(22) Filed: Dec. 27, 2019

(51) Int. Cl.
*B01D 3/10* (2006.01)
*B01D 11/02* (2006.01)
(Continued)

(52) U.S. Cl.
CPC ............. *C11B 7/0008* (2013.01); *B01D 3/10* (2013.01); *B01D 9/00* (2013.01); *B01D 11/028* (2013.01);
(Continued)

(58) Field of Classification Search
CPC .... B01D 17/02; B01D 11/04; B01D 11/0488; B01D 11/0492; B01D 3/10; B01D 3/106; B01D 3/108; B01D 11/02; B01D 11/0203; B01D 11/0215; B01D 11/028; B01D 11/0284; B01D 11/0288; B01D 11/0484; B01D 61/04; B01D 61/10; B01D 61/14; B01D 61/142; B01D 61/16; B01D 61/20; B01D 61/58; B01D 2257/702; B01D 2313/13; B01D 2313/50; B01D 2311/04; B01D 2311/26; B01D 2311/2699;
(Continued)

(56) References Cited

U.S. PATENT DOCUMENTS 9,649,349 B1 * 5/2017 Tucker .................... B01D 3/02
9,744,200 B1 * 8/2017 Tucker .................... A23L 27/10
(Continued)

FOREIGN PATENT DOCUMENTS

WO 2019034936 A2 2/2019

OTHER PUBLICATIONS

Patent Cooperation Treaty, Notification of Transmittal of the International Search Report and the Written Opinion of the International Searching Authority, or the Declaration, dated Mar. 25, 2020, Applicant: Cresco Labs LLC, Authorized Officer: Lee Young.

*Primary Examiner* — Joseph W Drodge
(74) *Attorney, Agent, or Firm* — Flener IP & Business Law; Zareefa B. Flener; Ayhan E. Mertogul (57) ABSTRACT

A method for post processing oil extracted from *cannabis* comprises the steps of placing the oil into a container at a first predetermined temperature for a first predetermined time during which the oil will separate into two parts comprising a high terpene (HT) liquid fraction and a high cannabinoid (HC) crystal fraction, heating the HT and HC fractions under a first predetermined level of vacuum at a second predetermined temperature for a second predetermined time, and heating the HC fraction to a third predetermined temperature for a third predetermined time. The steps further comprise adding a first predetermined quantity of the HT fraction back into the HC fraction to create a first mixture, adding a second predetermined quantity of benign terpenes into the first mixture to create a second mixture, and mixing the second mixture to create a finished mixture.

21 Claims, 4 Drawing Sheets

(51) Int. Cl.
*B01D 17/02* (2006.01)
*C11B 7/00* (2006.01)
*C11B 3/16* (2006.01)
*A61K 36/18* (2006.01)
*B01D 9/00* (2006.01)
*A61K 36/185* (2006.01)

(52) U.S. Cl.
CPC .......... *B01D 11/0288* (2013.01); *B01D 17/02* (2013.01); *C11B 3/16* (2013.01); *A61K 36/185* (2013.01)

(58) Field of Classification Search
CPC ........ B01D 9/00; A61K 36/00; A61K 36/185; C11B 1/10; C11B 1/108; C11B 3/16; C11B 7/00; C11B 7/0008; C11B 7/0041; C11B 7/0058; C11B 7/0066; C11B 1/104; C11B 3/001; C11B 3/006; C11B 3/008; B01F 1/00; B01F 1/0005; B01F 1/0038; B01F 3/0803; B01F 3/0811; B01F 3/0815; B01F 3/12; B01F 3/1207; B01F 3/1214; B01F 2003/125; B01F 2003/1257
USPC ......... 210/634, 776, 790; 366/348; 424/725; 554/8, 20, 175
See application file for complete search history.

(56) References Cited

U.S. PATENT DOCUMENTS

| | | | | |
|---|---|---|---|---|
| 10,155,176 | B1* | 12/2018 | Feuer | B01D 11/048 |
| 10,413,845 | B1* | 9/2019 | Tegen | A61K 36/185 |
| 10,414,709 | B1* | 9/2019 | Tegen | C07C 39/23 |
| 10,631,556 | B2* | 4/2020 | Franklin | A21D 13/44 |
| 2004/0147767 | A1 | 7/2004 | Whittle et al. | |
| 2017/0008870 | A1* | 1/2017 | Dibble | C07D 311/80 |
| 2018/0214790 | A1 | 8/2018 | Tucker | |
| 2018/0296616 | A1* | 10/2018 | Rivas | A61K 36/185 |
| 2018/0296617 | A1* | 10/2018 | Rivas | A61K 36/185 |
| 2019/0077781 | A1* | 3/2019 | Dijkstra | B01D 11/0296 |
| 2019/0153484 | A1* | 5/2019 | Bray | A61K 31/352 |
| 2019/0246591 | A1* | 8/2019 | Leo | B01D 11/0296 |
| 2020/0054702 | A1* | 2/2020 | Heller | A61K 36/185 |
| 2020/0056115 | A1* | 2/2020 | Vanaman | B01D 3/12 |
| 2020/0122052 | A1* | 4/2020 | Tucker | B01D 3/40 |
| 2020/0179269 | A1* | 6/2020 | Tamir | A61K 31/05 |

* cited by examiner

POST PROCESSING METHOD FOR *CANNABIS* OIL

FIELD OF THE INVENTION

The present invention relates to a method for post processing oil extracted from *cannabis* plants. More specifically, the present invention relates to a method for post processing that provides a full spectrum profile of cannabinoids and a high retention of terpenes.

BACKGROUND

Post processing techniques can be applied to oil extracted from *cannabis* plants to produce products having desirable formulations for intended uses. For example, it can be desirable for the post processed oil to have a high retention of terpenes, which are the aromatic oils produced by plants including *cannabis*. The terpenes not only provide the characteristic smells that people normally associate with the plants, but can also provide other beneficial health effects depending on use.

It can also be desirable for the post processed oil to have a full spectrum of cannabinoids, for example without limitation, tetrahydrocannabinol (THC), tetrahydrocannabinolic acid (THCA), cannabidiol (CBD), cannabinol (CBN), cannabichromene (CBC), and cannabigerol (CBG). Product formulations containing a full spectrum of cannabinoids are believed to be more effective for their intended uses than product formulations having a high concentration of only a single cannabinoid, for example, when used in medications for treating pain, insomnia, or depression.

Processes using hydrocarbons for extracting *cannabis* oil from the plants are well known in the art. One example process is commonly known as Butane hash oil extraction, which uses Butane to produce a product oil commonly known as Butane hash oil (BHO). Typical non-post processed extracted oil, for example, BHO, does not provide a high level of terpenes or a full spectrum of cannabinoids. The raw non-post processed oil can be improved by applying post processing techniques to the raw oil to achieve desired formulations for intended uses. Therefore, there is a need for post processing techniques that produce *cannabis* oil having a high level of terpenes and/or a full spectrum of cannabinoids.

SUMMARY OF THE INVENTION

According to one aspect of the invention, a method for post processing oil extracted from *cannabis* comprises the steps of placing the oil into a container at a first predetermined temperature for a first predetermined time during which the oil will separate into two parts comprising a high terpene (HT) liquid fraction and a high cannabinoid (HC) crystal fraction, heating the HT and HC fractions under a first predetermined level of vacuum at a second predetermined temperature for a second predetermined time, and heating the HC fraction to a third predetermined temperature for a third predetermined time. The method further comprises the steps of adding a first predetermined quantity of the HT fraction back into the HC fraction to create a first mixture, adding a second predetermined quantity of benign terpenes into the first mixture to create a second mixture, and mixing the second mixture to create a finished mixture.

According to another aspect of the invention, a method for post processing oil extracted from *cannabis* comprises the steps of placing the oil into a container at a first predetermined temperature in a range of between about 35° C. to about 50° C. for a first predetermined time in a range of between about 2 days to about 30 days, during which time the oil will separate into two parts comprising a high terpene (HT) liquid fraction and a high cannabinoid (HC) crystal fraction. The method further comprises the steps of heating the HT and HC fractions under a first predetermined level of vacuum in a range between about −25 inches of Hg to about −30 inches of Hg at a second predetermined temperature in a range between about 25° C. to about 50° C. for a second predetermined time in a range between about 48 hours to about 96 hours. The method still further comprises the step of heating the HC fraction to a third predetermined temperature in a range between about 80° C. to about 100° C. for a third predetermined time in a range between about 10 hours to about 14 hours. The method further comprises the steps of formulating a finished mixture by adding a first predetermined quantity of the HT fraction in a range of between about 10% to about 14% of the finished mixture by weight of the HT fraction back into the HC fraction to create a first mixture, adding a second predetermined quantity of benign terpenes in a range between about 5% to about 9% of the finished mixture by weight into the first mixture to create a second mixture, and mixing the second mixture while heating at a temperature range of between about 60° C. to about 90° C. for a time range of between about 15 minutes and about 30 minutes to create the finished mixture.

According to a further aspect of the invention, a method for post processing oil extracted from *cannabis* comprises the steps of placing the oil into a container at about 35° C. for a first predetermined time in a range of between about 3 days to about 10 days, during which time the oil will separate into two parts comprising a high terpene (HT) liquid fraction and a high cannabinoid (HC) crystal fraction, heating the HT and HC fractions under a vacuum level of about −28 inches of Hg at about 35° C. for about 72 hours, and heating the HC fraction about 95° C. for about 12 hours. The method further comprises the steps of adding about 12% of the finished mixture by weight of the HT fraction back into the HC fraction to create a first mixture, adding about 7% of the finished mixture by weight of benign terpenes into the first mixture to create a second mixture, and mixing the second mixture while heating at a temperature of about 75° C. for a minimum of about 20 minutes to create the finished mixture.

BRIEF DESCRIPTION OF THE DRAWINGS

Other aspects and advantages of the present invention will become apparent upon consideration of the following detailed description, wherein similar structures have similar reference numerals.

DETAILED DESCRIPTION

The following detailed embodiments presented herein are for illustrative purposes. That is, these detailed embodiments are intended to be exemplary of the present invention for the purposes of providing and aiding a person skilled in the pertinent art to readily understand how to make and use of the present invention.

The first step for producing *cannabis* oil having high terpene retention and a full spectrum of cannabinoids is to provide raw *cannabis* oil extracted by any means as may be known in the art, for example, by a hydrocarbon *cannabis* oil extraction process. In the context of *cannabis* oil extraction, a process starting with fresh frozen *cannabis* plants in contrast to plants that have been dried or heated produces a product known as live resin, which typically has a higher retention of terpenes than would result from plants that have been dried or heated.

One exemplary hydrocarbon *cannabis* oil extraction process suitable for use with the post processing techniques described hereinbelow utilizes liquid Butane as the hydrocarbon. Referring to the process flowchart of FIG. 1, at step 10 the exemplary process is executed with the aid of a chiller for the solvent tank that is set, for example, to a temperature range between about 0° C. and about −20° C. In another exemplary process the chiller is set to a temperature range between about −2° C. and about −15° C. In a further exemplary process the chiller is set to a temperature between about −5° C. and about −9° C., preferably at about −7° C.

Figure 1:
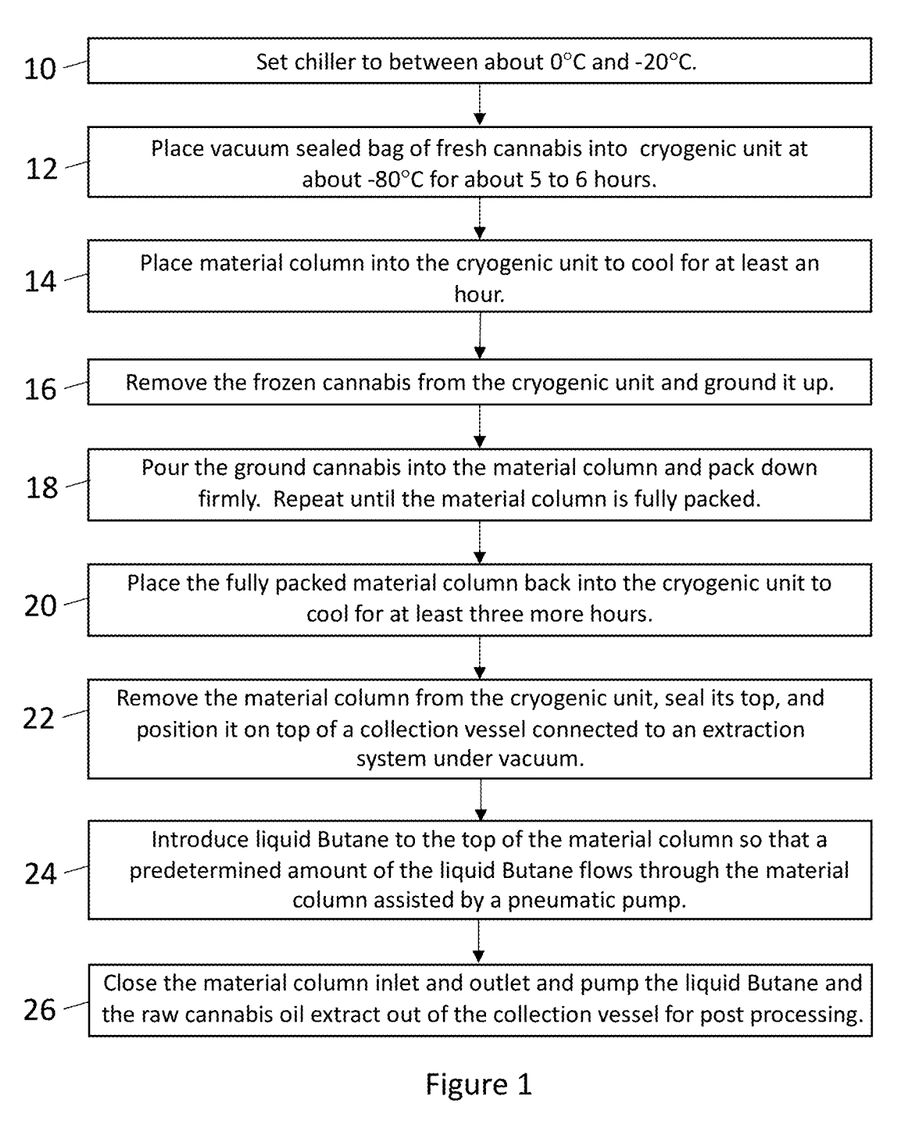
FIG. 1 is a process flowchart for a *cannabis* oil extraction process.

Before placing the fresh frozen *cannabis* into a closed loop system, where it is exposed to the liquid Butane, a vacuum sealed bag of the fresh frozen *cannabis* is placed into a cryogenic unit, for example, at a temperature of about −80° C. for about 5 to 6 hours at step 12. A material column, for example, a tube lined with a filtering cloth or a screen across a bottom end is also placed into the cryogenic unit and allowed to cool for at least an hour at step 14.

Still referring to FIG. 1, the bag of fresh frozen *cannabis* is removed from the cryogenic unit and the frozen *cannabis* is ground up, for example, by pounding with a mallet at step 16. At step 18, the ground *cannabis* is poured into a portion of the material column and packed down firmly. More ground *cannabis* is repeatedly poured into the material column and packed down firmly until the material column is considered to be fully packed, which occurs when about 1-2 inches are left unfilled at a top of the material column. At step 20, the fully packed material column can be placed back into the cryogenic unit to cool for at least three more hours.

At step 22, the fully packed material column is removed from the cryogenic unit, a top of the material column is sealed, and the material column is placed on top of a collection vessel that is connected to an extraction system under vacuum. A separate vacuum system is used to pull vacuum on the extraction system and therefore on an outlet of the material column. In one embodiment of the process, a vacuum, for example, of between about −25 and about −30 inches of Hg, and preferably of about −28 inches of Hg is established in the material column by the vacuum system.

At step 24, a liquid Butane supply is disposed in fluid communication with an inlet at the top of the material column so that a predetermined amount of the liquid Butane, for example, between about 1 pound and about 5 pounds of liquid Butane per pound of frozen *cannabis* biomass, preferably between about 2 pounds and about 4 pounds of liquid Butane per pound of frozen *cannabis* biomass, and more preferably about 3 pounds of liquid Butane per pound of frozen *cannabis* biomass, flows into the material column assisted by a pneumatic pump connected on the extraction system. After the predetermined amount of liquid Butane has flowed through the material column and into the collection vessel, at step 26 the inlet to and the outlet from the material column are closed, and the liquid Butane and the raw *cannabis* oil extract are pumped out of the collection vessel for post processing.

Two examples of post processing methods or techniques are described hereinbelow. Both of the post processing methods provide a *cannabis* oil formulation that has a high retention of terpenes and a full spectrum cannabinoid profile. In addition, both of the post processing methods inhibits further crystallization of THCA once the process is complete. Inhibiting further crystallization of THCA is imperative for vaporizer cartridges as it stops clogging of the device due to THCA crystalline being absent.

Post Processing Method—Example 1

A first step in a first exemplary method for post processing a quantity of raw *cannabis* oil extract acquired from the extraction process described hereinabove or by any other suitable process as known in the art is a crystallizing step. Referring to the process flowchart of FIG. 2, at step 30 the raw *cannabis* oil extract is placed into one or more containers, for example, one or more wide mouth mason jars, and left to stand at a first predetermined temperature, for example, in an oven, for a first predetermined time to begin a crystallization process.

Figure 2:
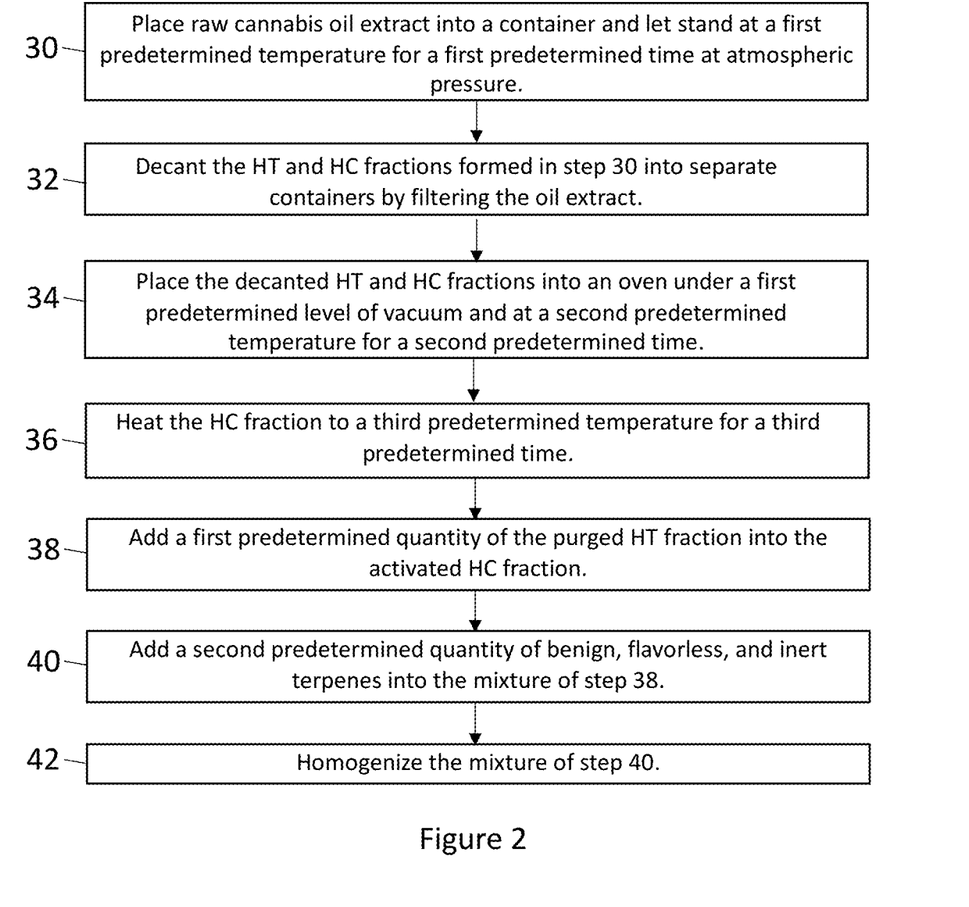
FIG. 2 is a process flowchart for a first example of a method for post processing a quantity of raw *cannabis* oil extract.

In one embodiment the first predetermined temperature is in a range of between about 30° C. to about 50° C. In another embodiment the first predetermined temperature is about 35° C. Both the first predetermined temperature and the first predetermined time may be dependent upon the particular strain of *cannabis* being processed. In one embodiment the first predetermined time is anywhere between about 2 days to about 30 days. In another embodiment the first predetermined time is in a range of between about 3 days to about 10 days. In a further embodiment the first predetermined time is in a range between about 4 days to about 7 days.

The crystallizing step in this embodiment is executed at atmospheric pressure. However, in other embodiments the crystallizing step may be executed at a pressure greater than or less than atmospheric pressure. After the predetermined time the *cannabis* oil extract will have separated into two parts comprising a high terpene (HT) liquid fraction on top and a high cannabinoid (HC) crystal fraction on bottom.

Referring again to FIG. 2, at step 32 the HT and HC fractions are decanted into separate containers, for example, by filtering the oil extract through a screen. In one embodiment the screen has apertures that are, for example, about 300 microns wide; however in other embodiments the filtering screen may have apertures that are larger or smaller then about 300 microns wide. The size of the apertures in the filtering screen may be dependent upon the strain of *cannabis* being processed. The HT liquid fraction passes through the screen and is collected in a container, for example, a beaker. The HC crystal fraction collects on the screen and is placed into a separate container.

At step 34, the decanted HT and HC fractions are vacuum oven purged. The decanted HT and HC fractions are placed into a vacuum oven under a first predetermined level of vacuum and at a second predetermined temperature for a second predetermined time to purge any hydrocarbons, for example Butane, remaining in the fractions.

In one embodiment, the first predetermined level of vacuum is in a range of between about −25 inches of Hg to about −30 inches of Hg. In another embodiment the first predetermined level of vacuum is about −28 inches of Hg. In one embodiment the second predetermined temperature is in a range of between about 25° C. to about 50° C. In another embodiment the second predetermined temperature is about 35° C. In one embodiment the second predetermined time is in a range between about 48 hours and about 96 hours. In another embodiment the second predetermined time is about 72 hours.

Once the purging has completed, at step 36 the container comprising the HC fraction is heated to a third predetermined temperature for a third predetermined time to activate the HC fraction. In one embodiment, the third predetermined temperature is in a range of between about 80° C. to about 100° C. In another embodiment the third predetermined temperature is about 95° C. In one embodiment the third predetermined time is in a range between about 10 hours and about 14 hours. In another embodiment the third predetermined time is about 12 hours.

As a practical consideration of heating glassware, for example, wide mouth mason jars as may be used in the first exemplary method for post-processing raw extracted *cannabis* oil, in an alternative embodiment step 36 may further include a brief ramp up time for reaching the third predetermined temperature. For example, in the alternative embodiment the HC fraction may first be heated to a lower temperature that is less than the third predetermined temperature and held there for a brief period of time, for example without limitation, about 15 minutes to about 30 minutes, to allow the glassware to heat up. Including the brief ramp up time of the alternative embodiment may be desirable because heating the glassware directly to the third predetermined temperature may risk cracking the glassware, which would be undesirably messy and expensive. Subsequently, the HC fraction is heated to the third predetermined temperature and held there until the time since being first heated to the lower temperature reaches the third predetermined time.

The activation step is meant to specifically decarboxylate cannabinoids such as CBDA and THCA that are comprised with a carboxyl group. Removal of the carboxyl group enables binding to CB1 and CB2 receptors. The CBDA is converted into CBD and the THCA is converted into "activated" THC. This activation is performed by the activating step outlined above.

If the activating step is executed correctly, activation of the HC fraction is evident from melting of the HC crystals as well as the off gassing of CO2. As the activating step progresses the HC fraction will start to become a homogenous oil mixture. The activating step is complete when there is no longer any CO2 off gassing from the HC fraction, meaning that the HC fraction should be fully activated. In a further embodiment, the activating step is preferably executed using a stir bar to stir the HC fraction while heating to ensure complete activation thereof.

After the activating step is complete, a formulation step completes the first exemplary post processing method. The formulation step comprises first and second adding steps and a final mixing step. At step 38, a first of two adding steps comprises adding a first predetermined quantity of the purged HT fraction into the now activated HC fraction. The amount of purged HT fraction added is determined based on the desired percentage of HT fraction by weight (% w) in the final mixture. At step 40 a second of two adding steps comprises adding a second predetermined quantity of benign, flavorless, and inert terpenes (BT fraction) into a mixture of the activated HC fraction and the purged HT fraction. The amount of BT fraction added is determined based on the desired percentage of BT fraction by weight (% w) in the final mixture.

Mathematically, the formula for deducing how much of the HT fraction and how much of the BT fraction are needed for adding in the two adding steps is simple to derive. For example, weighing the quantities of components in grams, one can derive a final formulated batch weight (FFBW) based on the desired percentages of the FFBW for the HT and BT fractions through the following progression of equations:

$$FFBW_{grams}=HC_{grams}+HT_{grams}+BT_{grams} \quad (1)$$

$$FFBW_{grams}-(HT_{grams}+BT_{grams})=HC_{grams} \quad (2)$$

$$FFBW_{grams}(1-(HT_{grams}+BT_{grams})/FFBW_{grams})=HC_{grams} \quad (3)$$

$$FFBW_{grams}(1-(HT_{\%w}+BT_{\%w}))=HC_{grams} \quad (4)$$

So, that $$FFBW_{grams}=HC_{grams}/(1-(HT_{\%w}+BT_{\%w})) \quad (5)$$

In one embodiment, the first predetermined quantity of the HT fraction is in a range between about 10% by weight (% w) to about 14% by weight (% w) of the completed mixture. In another embodiment the first predetermined quantity of the HT fraction is about 12% by weight (% w) of the completed mixture. In one embodiment the second predetermined quantity of the BT fraction is in a range between about 5% by weight (% w) to about 9% by weight (% w) of the completed mixture. In another embodiment the second predetermined quantity of the BT fraction is about 7% by weight (% w) of the completed mixture.

The amounts of the HT and BT fractions needed to achieve the desired first and second quantities thereof are computed by using equation 5 to first compute the FFBW based on the amount of the HC fraction. For example, assuming an amount of HC fraction of about 313.3 grams, and plugging in the desired percentages of the HT and BT fractions noted above, equation 5 becomes:

$$FFBW_{grams}=(313.3_{grams})/(1-(0.12+0.07)) \quad (6)$$

$$FFBW_{grams}=386.79_{grams} \quad (7)$$

Once the FFBW has been established, the weights of the HT and BT fractions needed to produce the desired final percentages of each by weight in the completed mixture are easily computed by multiplying the FFBW by each desired percentage. In this example, the required amount of the HT fraction to be added in the first adding step would therefore be computed as equal to $(0.12)*(386.79_{grams})=46.41_{grams}$.

After the first of the two adding steps is complete, the second of the two adding steps comprises adding the second predetermined quantity of benign, flavorless, and inert terpenes (BT fraction) into the mixture of the activated HC and the first predetermined quantity of HT fraction resulting from the first adding step. In this example, the required amount of BT fraction to be added in the second adding step would be computed as equal to $(0.07)*(386.79_{grams})=27.08_{grams}$.

After the second of the two adding steps is complete, a homogenizing step at step 42 comprises mixing the activated HC fraction, the first predetermined quantity of the HT fraction, and the second predetermined quantity of the BT fraction. In one embodiment, the homogenizing step comprises mixing using a stirrer on a hotplate. In this embodiment, homogenization of the final formulated solution should be performed at a temperature range of between about 60° C. to about 90° C. and should be stirred on the hot plate for a time range of between about 15 minutes and about 30 minutes. In another embodiment homogenization of the final formulated solution should be performed at a temperature of about 75° C. and should be stirred on the hot plate for a minimum of about 20 minutes.

The resultant *cannabis* oil formulation resulting from the first method described hereinabove for example 1 comprises both a high level of terpene concentration and a full spectrum cannabinoid profile. As evident from the data in Table 1, depending on the *cannabis* strain used for extraction of the raw non-post-processed *cannabis* oil extract, the first method of example 1 results in detectable levels of as many as four different cannabinoids in addition to a high terpene concentration of at least 4.7% wt (by weight).

TABLE 1

Formulation of post processed cannabis oil for the first method

| Strain | THC % wt | THCA % wt | CBD % wt | CBN % wt | CBC % wt | CBG % wt | Terps % wt |
|---|---|---|---|---|---|---|---|
| A | 76.6 | 4.4 | ND | ND | ND | 1.2 | 5.4 |
| B | 60.7 | 7.5 | ND | ND | ND | 1.1 | 7.8 |
| C | 59.9 | 9.7 | ND | ND | ND | ND | 4.8 |
| D | 61.5 | 9.9 | ND | ND | ND | 1.9 | 5.1 |
| E | 64.6 | 4.2 | ND | ND | ND | 1.1 | 4.7 |
| F | 41.7 | 14.6 | ND | ND | 0.8 | 2.1 | 5.4 |

ND = Not detected

Post Processing Method—Example 2

A second exemplary method for post processing a quantity of raw *cannabis* oil extract acquired from the extraction process described hereinabove or by any other suitable process as known in the art is described hereinbelow. While the first exemplary method described hereinabove works very well for the post-processing of extracted *cannabis* oil, as will be seen the second exemplary method has some advantages over the first exemplary method.

A first step in the second exemplary method for post processing is an activation step. One advantage of the second exemplary method over the first exemplary method is that the activation step in the second exemplary method is executed within a single pressure rated vessel (PRV) without separation of the HC and HT fractions, and without the need for one or more containers, for example, one or more wide mouth mason jars. Another advantage of the second exemplary method is that the processing time for activation and purging of the oil is reduced from a typical range of between about 9 days to 12 days for the first exemplary method to a typical range of about 5 days for the second exemplary method.

Further, the second exemplary method does not include steps for formulation that are included in the first exemplary method. Elimination of the formulation step further reduces the total processing time, and elimination of the separation of the HC and HT fractions eliminates waste of HT fraction that goes unused in the final formulation.

The typical yield of oil post processed by the second exemplary method is increased from the typical yield of oil post processed by the first exemplary method (for example, the yield was 3.3% by weight for the second exemplary method vs 2.6% by weight for the first exemplary method, representing a 27% increase in yield). The average level of Terpenes in the oil post processed by the second exemplary method is increased to about 4.1% from an average level of Terpenes of about 3.3% yielded by the first exemplary method, while the average % THC in the post processed oil from both methods remains about the same (decreasing slightly from to 77.4% for the second exemplary method from about 79.5% for the first exemplary method).

Additionally, the second exemplary method requires less actual process steps and far fewer container transfers than the first exemplary method (as will be seen hereinbelow). Fewer process steps and fewer container transfers can mean less losses due to process, losses due to transfer, or even losses due to breakage of the one or more containers utilized in the first exemplary method. Less losses translates to less lost revenues. Further, whereas scaling the first exemplary method up to larger production quantities of oil would require using more and more containers and would be practically far more difficult, the second exemplary method is more easily scalable for processing larger production quantities of oil simply by using a larger pressure rated vessel (PRV).

Figure 3:
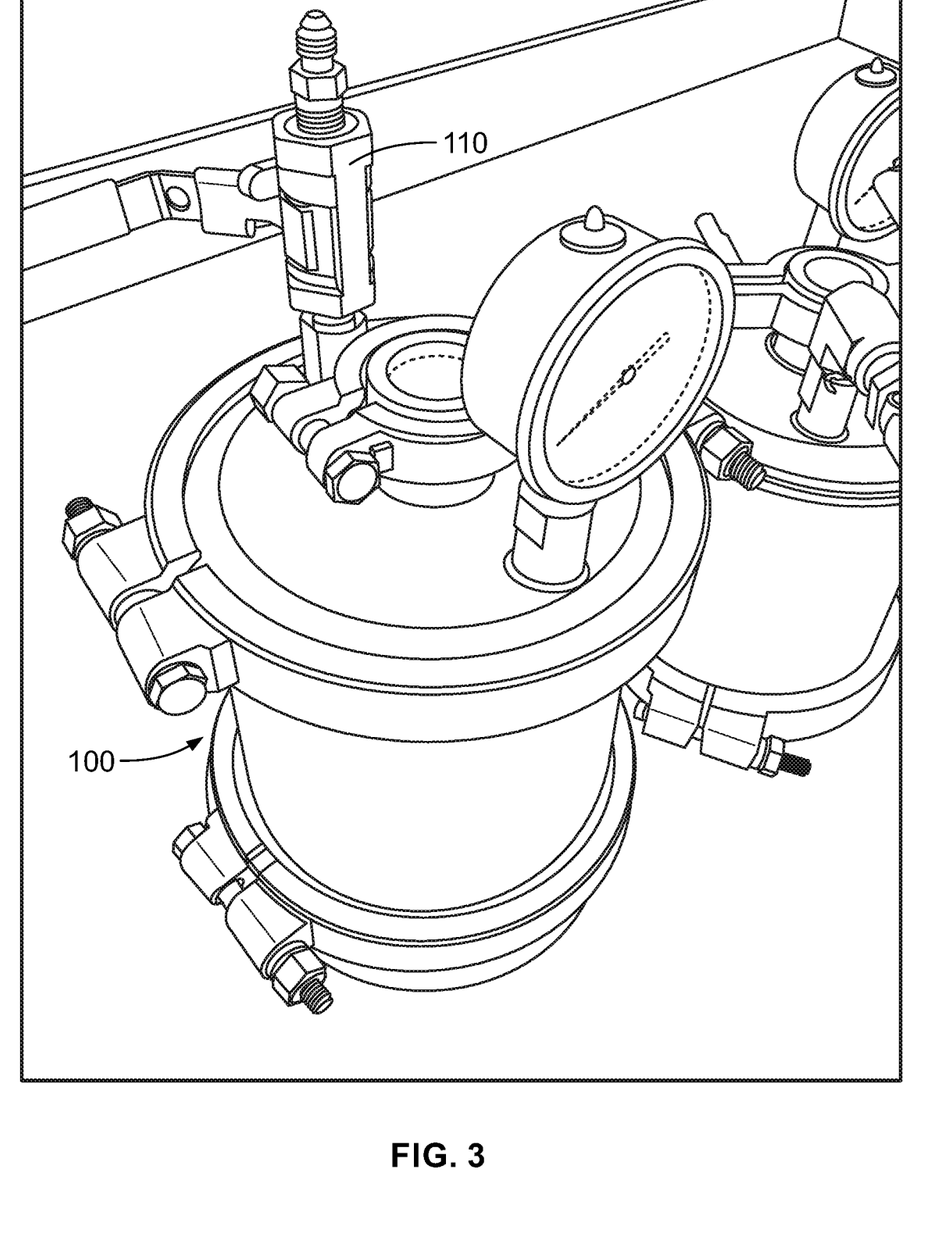
FIG. 3 is an embodiment of a pressure rated vessel (PRV) of the sort suitable for use in the present invention.

Returning to the activation step, the raw *cannabis* oil is placed into a pressure rated vessel (PRV) that can hold fluids, for example, hydrocarbons under pressure. In one embodiment the PRV 100 can be an unjacketed vessel as illustrated in FIG. 3 meaning that the primary pressure retaining structure of the PRV has no secondary jacket around it. However, in another embodiment, the PRV can be a jacketed vessel meaning that the primary pressure retaining structure of the PRV is at least partially enclosed within an outer jacket forming a secondary volume within the outer jacket.

In one embodiment the secondary volume may comprise a vacuum. In another embodiment the outer jacket may be configured to hold elevated pressures like the primary pressure retaining structure of the PRV. In one embodiment, the secondary volume has one or more inlet ports and/or valves and one or more outlet ports and/or valves, thereby allowing the circulation of a secondary fluid through the jacket. The secondary fluid could be used, for example, to provide heating and/or cooling to the PRV. In one embodiment, for example, circulation of superheated steam or other heated fluid through the outer volume can heat the contents of the contents of the primary pressure retaining structure of the PRV without placing the PRV into an oven.

Figure 4:
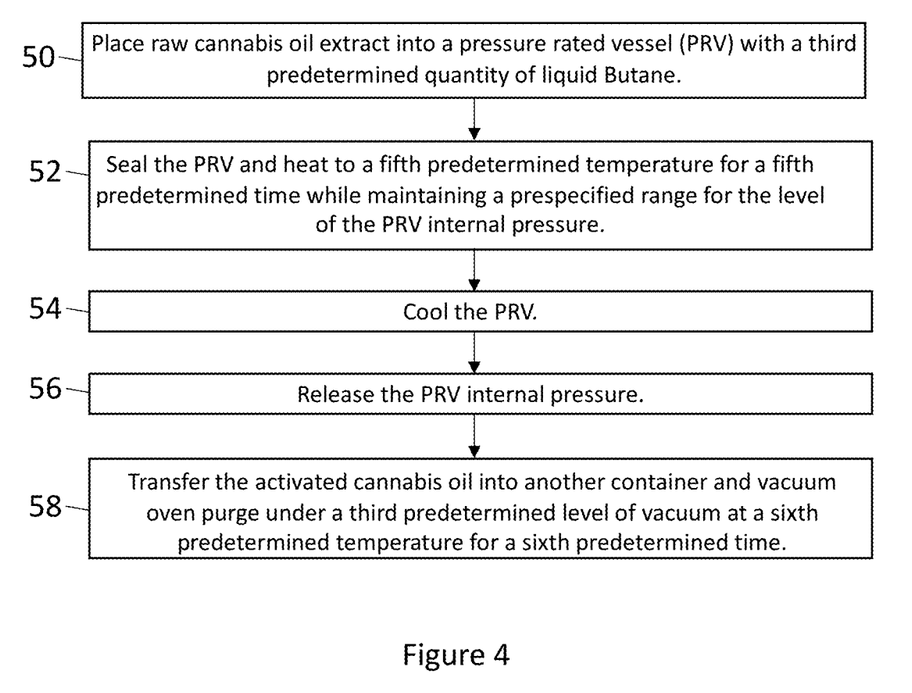
FIG. 4 is a process flowchart for a second example of a method for post processing a quantity of raw *cannabis* oil extract.

Referring to the process flowchart of FIG. 4, at step 50 in the activation step, the raw *cannabis* oil extract is placed inside the PRV 100 with a third predetermined quantity of liquid Butane. If an insufficient amount of liquid Butane is used, the oil extract/Butane mixture can stick to the inside of the PRV 100 and burn, which is highly undesirable. Therefore, the objective is to use copious amounts of liquid Butane, so as to objectively suspend the raw *cannabis* oil extract in a liquid Butane solution.

In one exemplary embodiment, the third predetermined quantity of liquid Butane has between about 3 times and about 10 times the volume of the raw *cannabis* oil extract. In another embodiment the third predetermined quantity of liquid Butane has at least about 5 times the volume of the raw *cannabis* oil extract.

After adding the Butane to the PRV 100, at step 52 the vessel is sealed shut and heated to a fifth predetermined temperature for a fifth predetermined time to activate the cannabinoids THC or CBD. The activation step is meant to specifically decarboxylate cannabinoids such as CBDA and THCA that are comprised with a carboxyl group. The CBDA is converted into CBD and the THCA is converted into "activated" THC.

In one embodiment, the PRV 100 is heated in an oven at the fifth predetermined temperature in a range of between about 60° C. to about 235° C. In another embodiment the fifth predetermined temperature is in a range of between about 60° C. to about 100° C. In yet another embodiment, the fifth predetermined temperature is in a range of between about 60° C. to about 75° C., and preferably at about of 68° C.

In one embodiment, the PRV 100 is heated in an oven at the fifth predetermined temperature for a fifth predetermined time in a range of between about 24 to about 60 hours. In another embodiment the fifth predetermined time is in a range of between about 30 to about 54 hours, and in yet another embodiment the fifth predetermined time is a minimum of about 48 hours.

Sealing the PRV 100 shut and heating it at step 52 to the fifth predetermined temperature for the fifth predetermined time results in an increase of the internal pressure of the PRV 100, for example, due directly to the heating and also due to an increase in pressure resulting from the decarboxylation reaction. Step 52 includes controlling the level of the internal pressure in the PRV 100 to be at about a predetermined pressure or at least to be maintained within a predetermined range of pressures.

The level of the internal pressure in the PRV 100 is controlled by controlling the amount of heat applied to the PRV 100 in combination with controlling the total volume of the raw *cannabis* oil extract and the liquid Butane disposed inside the PRV 100. As a step in controlling the total volume, the PRV 100 is only partially filled with the raw *cannabis* oil extract and the liquid Butane. For example, in one embodiment, the PRV 100 is filled to about 50% volume capacity with the raw *cannabis* oil extract and the liquid Butane. In other exemplary embodiments, the PRV 100 is filled to less than 50% volume capacity, for example to about 40%, about 30%, about 20% volume capacity, or less with the raw *cannabis* oil extract and the liquid Butane. In yet other exemplary embodiments, the PRV 100 is filled to about 60%, about 70%, or about 80% volume capacity with the raw *cannabis* oil extract and the liquid Butane. As a safety precaution and to allow for operable control of the internal pressure of the PRV 100, the PRV 100 is not filled past about 80% volume capacity with the raw *cannabis* oil extract and the liquid Butane.

Execution of step 52 with controlled application of heat to a controlled total volume of the raw *cannabis* oil extract and the liquid Butane as described hereinabove, results, in one embodiment, in a controlled increase in internal pressure of the PRV 100 to a pressure between about 20 psi and about 450 psi above atmospheric pressure. In another embodiment, the internal pressure of the PRV 100 is controllably increased to a pressure between about 150 psi and about 350 psi above atmospheric pressure. In yet another embodiment, the internal pressure of the PRV 100 is controllably increased to a pressure between about 150 psi and about 250 psi above atmospheric pressure, and preferably to a pressure of about 200 psi above atmospheric pressure. The controlled application of heat to the PRV 100 to control the temperature and the internal pressure of the PRV 100 may be through application of heat to an unjacketed PRV from an external heat source, or through application of heat to a jacketed PRV using the circulation of a heated secondary fluid through the jacket as described above, or through a combination of heat applied to a jacketed PRV from an external heat source and using the circulation of a heated secondary fluid through the jacket.

After heating for the fifth predetermined time, in one embodiment the PRV 100 is cooled at step 54. In one embodiment, for example, the PRV 100 is cooled by placing the PRV 100 on a cold surface, for example, on ice for a brief time, for example about 10 min, and subsequently allowing it to rest at room temperature, for example, for about an additional 15 minutes. After the cooling step described above the PRV 100 has an internal pressure that can still be above atmospheric pressure. For example, the internal pressure typical of the cooling step described above can be about 110 psi above atmospheric pressure. After cooling the PRV 100 is released of its internal pressure at step 56, for example, by opening the valve 110. In other embodiments the PRV 100 is cooled via other sequences of times and temperatures to the point where the PRV 100 is cool enough for safe release of its internal pressure by opening of the valve 110.

The contents of the PRV 100, now comprising activated *cannabis* oil are transferred into another container at step 58 and vacuum oven purged under a third predetermined level of vacuum held steady at a sixth predetermined temperature for a sixth predetermined time. In one embodiment, the third predetermined level of vacuum is in a range of between about −25 inches of Hg and about −30 inches of Hg. In another embodiment the third predetermined level of vacuum is about −28 inches of Hg. In one embodiment the sixth predetermined temperature is in a range of between about 35° C. and about 50° C. In another embodiment the sixth predetermined temperature is about 48° C. In one embodiment the sixth predetermined time is in a range of between about 48 hours to about 120 hours. In another embodiment the sixth predetermined time is about 72 hours.

The resultant *cannabis* oil formulation resulting from the second method described hereinabove for example 2 comprises both a high level of terpene concentration and a full spectrum cannabinoid profile. As evident from the data in Table 2, depending on the *cannabis* strain used for extraction of the raw non-post-processed *cannabis* oil extract, the second method of example 2 results in detectable levels of at least 5 different cannabinoids in addition to a high terpene concentration of at least 4.88% wt (by weight). Referring to the data in Table 3 representative of known conventional methods, the second method results in an unprecedented amount of terpenes in the *cannabis* oil when compared to the known conventional methods.

TABLE 2

Formulation of post processed cannabis oil for the second method

| Strain | THC % wt | THCA % wt | CBD % wt | CBN % wt | CBC % wt | CBG % wt | Terps % wt |
|---|---|---|---|---|---|---|---|
| G | 61.41 | ND | 0.15 | 0.34 | 3.09 | 1.97 | 10.35 |
| H | 62.78 | 1.05 | ND | 0.35 | 0.98 | 1.22 | 8.27 |
| I | 65.38 | 2.03 | 0.16 | 0.1 | 0.69 | 2.48 | 9.34 |
| J | 70.44 | ND | 0.24 | 0.4 | 1.04 | 0.88 | 6.48 |
| K | 71.41 | ND | 0.17 | 0.42 | 1.29 | 1.8 | 4.88 |
| L | 63.8 | 0.75 | 0.13 | 3.5 | 0.41 | 1.55 | 8.06 |

ND = Not detected

TABLE 3

Results for formulations of post processed cannabis oil from known conventional methods

| Strain | THC % wt | THCA % wt | CBD % wt | CBN % wt | CBC % wt | CBG % wt | Terps % wt |
|---|---|---|---|---|---|---|---|
| M | 82.8 | ND | ND | ND | NT | 2.6 | 0.03 |
| N | 79.3 | ND | ND | ND | NT | 1.6 | 0.07 |
| O | 83.1 | ND | ND | ND | NT | 2.7 | 0.07 |

TABLE 3-continued

Results for formulations of post processed cannabis oil from known conventional methods

| Strain | THC % wt | THCA % wt | CBD % wt | CBN % wt | CBC % wt | CBG % wt | Terps % wt |
|--------|----------|-----------|----------|----------|----------|----------|------------|
| P | 83.6 | ND | ND | ND | NT | 2.4 | 0.83 |
| Q | 83.8 | ND | ND | ND | 1.4 | 2.1 | 0.06 |
| R | 84.3 | ND | ND | ND | 0.89 | 2.1 | 0.04 |

ND = Not detected,
NT = Not Tested

Those skilled in the art will appreciate that the invention described herein is susceptible to variations and modifications other than those specifically described, and that each embodiment is also provided with features that may be applicable to other embodiments. It is to be understood that the invention includes all such variations and modifications that fall within its spirit and scope. The invention also includes all the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

INDUSTRIAL APPLICABILITY

The method for post processing *cannabis* oil can be used by or in industry to produce *cannabis* oil having a high level of terpenes and/or a full spectrum of cannabinoids. The method comprises placing the oil into a container at a first predetermined temperature for a first predetermined time during which the oil will separate into two parts comprising a high terpene (HT) liquid fraction and a high cannabinoid (HC) crystal fraction. The HT and HC fractions are heated under a first predetermined level of vacuum at a second predetermined temperature for a second predetermined time, and heated to a third predetermined temperature for a third predetermined time. A first predetermined quantity of the HT fraction is added back into the HC fraction to create a first mixture, and a second predetermined quantity of benign terpenes is added into the first mixture to create a second mixture, which is further mixed to create a finished mixture.

Numerous modifications to the present invention will be apparent to those skilled in the art in view of the foregoing description. It is not desired to limit the invention to the exact construction and operation shown and described, and accordingly, all suitable modifications and equivalents may be resorted to, falling within the scope of the invention. Accordingly, this description is to be construed as illustrative only of the principles of the invention and is presented for the purpose of enabling those skilled in the art to make and use the invention and to teach the best mode of carrying out same. The exclusive rights to all modifications which come within the scope of the appended claims are reserved. All patents, patent publications and applications, and other references cited herein are incorporated by reference herein in their entirety.

We claim:

1. A method for post processing oil extracted from *cannabis*, the method comprising the steps of:
    placing the oil into a container at a first predetermined temperature for a first predetermined time during which the oil separates into two parts comprising a high terpene (HT) liquid fraction and a high cannabinoid (HC) crystal fraction;
    a first heating step comprising heating the HT and HC fractions under a first predetermined level of vacuum at a second predetermined temperature for a second predetermined time;
    a second heating step comprising heating the HC fraction to a third predetermined temperature for a third predetermined time;
    a first adding step comprising adding a first predetermined quantity of the HT fraction back into the HC fraction to create a first mixture;
    a second adding step comprising adding a predetermined quantity of benign terpenes into the first mixture to create a second mixture; and
    mixing the second mixture to create a finished mixture.

2. The method of claim 1, wherein the first predetermined temperature is in a range of between about 35° C. to about 50° C.

3. The method of claim 2, wherein the first predetermined temperature is about 35° C.

4. The method of claim 1, wherein the first predetermined time is in a range of between about 2 days to about 30 days.

5. The method of claim 4, wherein the first predetermined time is in a range of between about 3 days to about 10 days.

6. The method of claim 5, wherein the first predetermined time is in a range of between about 4 days to about 7 days.

7. The method of claim 1, wherein the first predetermined level of vacuum is in a range of between about −25 inches of Hg to about −30 inches of Hg, the second predetermined temperature is in a range of between about 25° C. to about 50° C., and the second predetermined time is in a range of between about 48 hours to about 96 hours.

8. The method of claim 7, wherein the first predetermined level of vacuum is about −28 inches of Hg, the second predetermined temperature is about 35° C., and the second predetermined time is about 72 hours.

9. The method of claim 1, wherein the third predetermined temperature is in a range of between about 80° C. to about 100° C., and the third predetermined time is in a range of between about 10 hours to about 14 hours.

10. The method of claim 9, wherein the third predetermined temperature is about 95° C., and the third predetermined time is about 12 hours.

11. The method of claim 1, wherein the predetermined quantity of the HT fraction is in a range of between about 10% to about 14% of the finished mixture by weight.

12. The method of claim 11, wherein the quantity of the HT fraction is about 12% of the finished mixture by weight.

13. The method of claim 1, wherein the predetermined quantity of the benign terpenes is in a range of between about 5% to about 9% of the finished mixture by weight.

14. The method of claim 13, wherein the predetermined quantity of the benign terpenes is about 7% of the finished mixture by weight.

15. The method of claim 1, wherein the mixing step further comprises mixing the second mixture while heating at a temperature range of between about 60° C. to about 90° C. for a time range of between about 15 minutes and about 30 minutes.

16. The method of claim 15, wherein the mixing step further comprises mixing the second mixture while heating at a temperature of about 75° C. for a minimum of about 20 minutes.

17. The method of claim 1, wherein
the first predetermined temperature is in a range of between about 35° C. to about 50° C. and
the first predetermined time is in a range of between about 2 days to about 30 days, during which time the oil separates into two parts comprising a high terpene (HT) liquid fraction and a high cannabinoid (HC) crystal fraction;
the first predetermined level of vacuum is in a range of between about −25 inches of Hg to about −30 inches of Hg, the second predetermined temperature is in a range of between about 25° C. to about 50° C., and the second predetermined time is in a range of between about 48 hours to about 96 hours
the third predetermined temperature is in a range of between about 80° C. to about 100° C. and the third predetermined time is in a range of between about 10 hours to about 14 hours;
the predetermined quantity of the HT fraction is in a range of between about 10% to about 14% of the finished mixture by weight;
the predetermined quantity of the benign terpenes is in a range of between about 5% to about 9% of the finished mixture by weight; and
the mixing step further comprises mixing the second mixture while heating at a temperature range of between about 60° C. to about 90° C. for a time range of between about 15 minutes and about 30 minutes; and wherein
the *cannabis* oil formulation comprises a level of terpene concentration of at least 4.7% by weight.

18. The method of claim 1, wherein
the first predetermined temperature is in a range of between about 35° C. to about 50° C. and
the first predetermined time is in a range of between about 2 days to about 30 days, during which time the oil separates into two parts comprising a high terpene (HT) liquid fraction and a high cannabinoid (HC) crystal fraction;
the first predetermined level of vacuum is in a range of between about −25 inches of Hg to about −30 inches of Hg, the second predetermined temperature is in a range of between about 25° C. to about 50° C., and the second predetermined time is in a range of between about 48 hours to about 96 hours
the third predetermined temperature is in a range of between about 80° C. to about 100° C. and the third predetermined time is in a range of between about 10 hours to about 14 hours;
the predetermined quantity of the HT fraction is in a range of between about 10% to about 14% of the finished mixture by weight;
the predetermined quantity of the benign terpenes is in a range of between about 5% to about 9% of the finished mixture by weight; and
the mixing step further comprises mixing the second mixture while heating at a temperature range of between about 60° C. to about 90° C. for a time range of between about 15 minutes and about 30 minutes; and wherein
the *cannabis* oil formulation comprises detectable levels of four different cannabinoids.

19. The method of claim 1, wherein
the first predetermined temperature is in a range of between about 35° C. to about 50° C. and
the first predetermined time is in a range of between about 2 days to about 30 days, during which time the oil separates into two parts comprising a high terpene (HT) liquid fraction and a high cannabinoid (HC) crystal fraction;
the first predetermined level of vacuum is in a range of between about −25 inches of Hg to about −30 inches of Hg, the second predetermined temperature is in a range of between about 25° C. to about 50° C., and the second predetermined time is in a range of between about 48 hours to about 96 hours
the third predetermined temperature is in a range of between about 80° C. to about 100° C. and the third predetermined time is in a range of between about 10 hours to about 14 hours;
the predetermined quantity of the HT fraction is in a range of between about 10% to about 14% of the finished mixture by weight;
the predetermined quantity of the benign terpenes is in a range of between about 5% to about 9% of the finished mixture by weight; and
the mixing step further comprises mixing the second mixture while heating at a temperature range of between about 60° C. to about 90° C. for a time range of between about 15 minutes and about 30 minutes; and wherein
the *cannabis* oil formulation comprises a level of terpene concentration of at least 4.7% by weight and detectable levels of four different cannabinoids.

20. A method for post processing oil extracted from *cannabis*, the method comprising the steps of:
placing the oil into a container at a first predetermined temperature in a range of between about 35° C. to about 50° C. for a first predetermined time in a range of between about 2 days to about 30 days, during which time the oil separates into two parts comprising a high terpene (HT) liquid fraction and a high cannabinoid (HC) crystal fraction;
a first heating step comprising heating the HT and HC fractions under a first predetermined level of vacuum in a range of between about −25 inches of Hg to about −30 inches of Hg at a second predetermined temperature in a range of between about 25° C. to about 50° C. for a second predetermined time in a range of between about 48 hours to about 96 hours;
a second heating step comprising heating the HC fraction to a third predetermined temperature in a range of between about 80° C. to about 100° C. for a third predetermined time in a range of between about 10 hours to about 14 hours;
a first adding step in formulating a finished mixture, the first adding step comprising adding a predetermined quantity of the HT fraction in a range of between about 10% to about 14% of the finished mixture by weight of the HT fraction back into the HC fraction to create a first mixture;
a second adding step comprising adding a predetermined quantity of benign terpenes in a range of between about 5% to about 9% of the finished mixture by weight into the first mixture to create a second mixture; and
mixing the second mixture while heating at a temperature range of between about 60° C. to about 90° C. for a time range of between about 15 minutes and about 30 minutes to create the finished mixture.

21. A method for post processing oil extracted from *cannabis*, the method comprising the steps of:

placing the oil into a container at about 35° C. for a first predetermined time in a range of between about 3 days to about 10 days, during which time the oil separates into two parts comprising a high terpene (HT) liquid fraction and a high cannabinoid (HC) crystal fraction;

a first heating step comprising heating the HT and HC fractions under a vacuum level of about −28 inches of Hg at about 35° C. for about 72 hours;

a second heating step comprising heating the HC fraction about 95° C. for about 12 hours;

a first adding step in formulating a finished mixture, the first adding step comprising adding about 12% of the finished mixture by weight of the HT fraction back into the HC fraction to create a first mixture;

a second adding step comprising adding about 7% of the finished mixture by weight of benign terpenes into the first mixture to create a second mixture; and mixing the second mixture while heating at a temperature of about 75° C. for a minimum of about 20 minutes to create the finished mixture.

\* \* \* \* \*